United States Patent [19]

Buechel et al.

[11] Patent Number: 4,738,254
[45] Date of Patent: Apr. 19, 1988

[54] POSITIONER FOR SURGICAL INSTRUMENTS

[75] Inventors: Frederick F. Buechel, South Orange; Michael J. Pappas, Caldwell, both of N.J.

[73] Assignee: Biomedical Engineering Trust, S. Orange, N.J.

[21] Appl. No.: 587,263

[22] Filed: Mar. 7, 1984

Related U.S. Application Data

[63] Continuation-in-part of Ser. No. 336,095, Dec. 31, 1981, abandoned.

[51] Int. Cl.⁴ ................................................. A61F 5/04
[52] U.S. Cl. ............................ 128/92 VW; 128/92 VD
[58] Field of Search .............. 128/92 H, 92 R, 303 R, 128/42 E, 92 VW, 92 VV, 92 VY, 92 V, 92 VD

[56] References Cited

U.S. PATENT DOCUMENTS

| | | | |
|---|---|---|---|
| 4,457,307 | 7/1984 | Stillwell | 128/92 H |
| 4,474,177 | 10/1984 | Whiteside | 128/92 H |
| 4,487,203 | 12/1984 | Androphy | 128/92 H |
| 4,502,483 | 3/1985 | Lacey | 128/92 H |
| 4,524,766 | 6/1985 | Petersen | 128/92 H |

OTHER PUBLICATIONS

Hungerford et al., "Precise Bone Cuts Everytime", Howmedica, Rutherford, N.J., 1980.

Primary Examiner—C. Fred Rosenbaum
Assistant Examiner—C. Reilly
Attorney, Agent, or Firm—Carella, Byrne, Bain & Gilfillan

[57] ABSTRACT

A positioner for positioning a surgical instrument which acts as a guide for a cutting instrument which produces a surgical cut in an anatomical structure; in one embodiment the positioner positions a surgical instrument which acts as a guide for the cutting instrument at a predetermined position with respect to a previously resected surface whereby a further resection is made at a predetermined position with respect to the previously resected surface; and in a further embodiment the positioner acts as an adaptor for a surgical instrument which aids in producing surgical sections thereby allowing the surgical instrument to produce surgical cuts at various predetermined positions relative to a previous surgical cut made at one of several levels.

1 Claim, 3 Drawing Sheets

POSITIONER FOR SURGICAL INSTRUMENTS

RELATED CASE

This application is a continuation-in-part of our prior application Ser. No. 336,095, filed Dec. 31, 1981 for POSITIONER FOR SURGICAL INSTRUMENTS now abandoned.

BACKGROUND OF THE INVENTION (1) Field of the Invention

During various surgical procedures involving invasion of anatomical members, e.g. the reaction of bone, it is often desirable to produce bores, cuts or resections that are at a predetermined orientation with and at a predetermined distance from some reference surface, axis or point, e.g. a previously resected surface. This invention relates to apparatus, referred to as a positioner, for positioning surgical instruments which act as guides for surgical instruments including cutting instruments which produce the surgical invasions, e.g. anatomical structure resections such as bone resections. It has been found that such positioners increase the accuracy of placement of surgical instruments thereby improving the quality of the surgical procedure.

(2) Description of the Prior Art

While various surgical instruments which act as guides for other surgical instruments are known to the art, it is believed that adequate positioners for such surgical instruments are not known to the art. Further, as is known to those skilled in the art, prosthetic devices, such as prosthetic knee joints, ankle joints, shoulder joints, finger joints, etc., have become increasingly sophisticated. Therefore more sophisticated surgical procedures for implantation are required. These more sophisticated surgical procedures require, inter alia, establishment of more accurate reference axes, planes and surfaces and to that end that bone bores, cuts or resections to be more accurately made than before. Hence, new positioning apparatus are required to more accurately position the surgical instruments which act as guides for the cutting instruments if the more accurate placement of surgical bores, cuts or resections is to be made.

Accordingly, there exists a need in the art for improved instrumentation, such as an improved positioner, for positioning surgical instruments which act as guides for producing more accurately placed surgical bores, cuts or resections. It is the object of the present invention to provide such improved positioners.

SUMMARY OF THE INVENTION

The foregoing object and others not enumerated are achieved by the positioner of the present invention, one embodiment of which may include a means for establishing an axial or planar reference with respect to an anatomical member to be surgically invaded and a body means adjustably secured to the means for establishing a reference, the body means defining a guide for a surgical instrument utilized to surgically invade the anatomical member.

BRIEF DESCRIPTION OF THE DRAWINGS

A more complete understanding of the present invention may be had from the following detailed description of a preferred embodiment thereof, particularly when read in light of the accompanying drawings, wherein.

DETAILED DESCRIPTION

As set out above, this invention relates to positioners for surgical instruments. The following detailed description of a preferred embodiment is made in the context of an improved femoral resection guide. Its use is disclosed in the context of femoral resection incidental to a total knee replacement.

A total knee replacement instrumentation system utilizing among other instruments, the improved femoral resection guide and femoral guide positioner of the present invention, is described in the brochure entitled "N.J. Knee Instrumentation System: Biomechanical and Surgical Rationale" by Michael J. Pappas, Ph.D. and Frederick F. Buechel, M.D., published in June 1983 by DePuy Division of Boehringer Manheim Corporation of Warsaw, Ind., and also, more generally, in the Surgical Procedure set forth in the publication entitled "New Jersey knee Surgical Procedures Manual" by Frederick F. Buechel, M.D. also by DePuy. This publication is incorporated herein by reference as if fully set forth herein at length.

Figure 1:
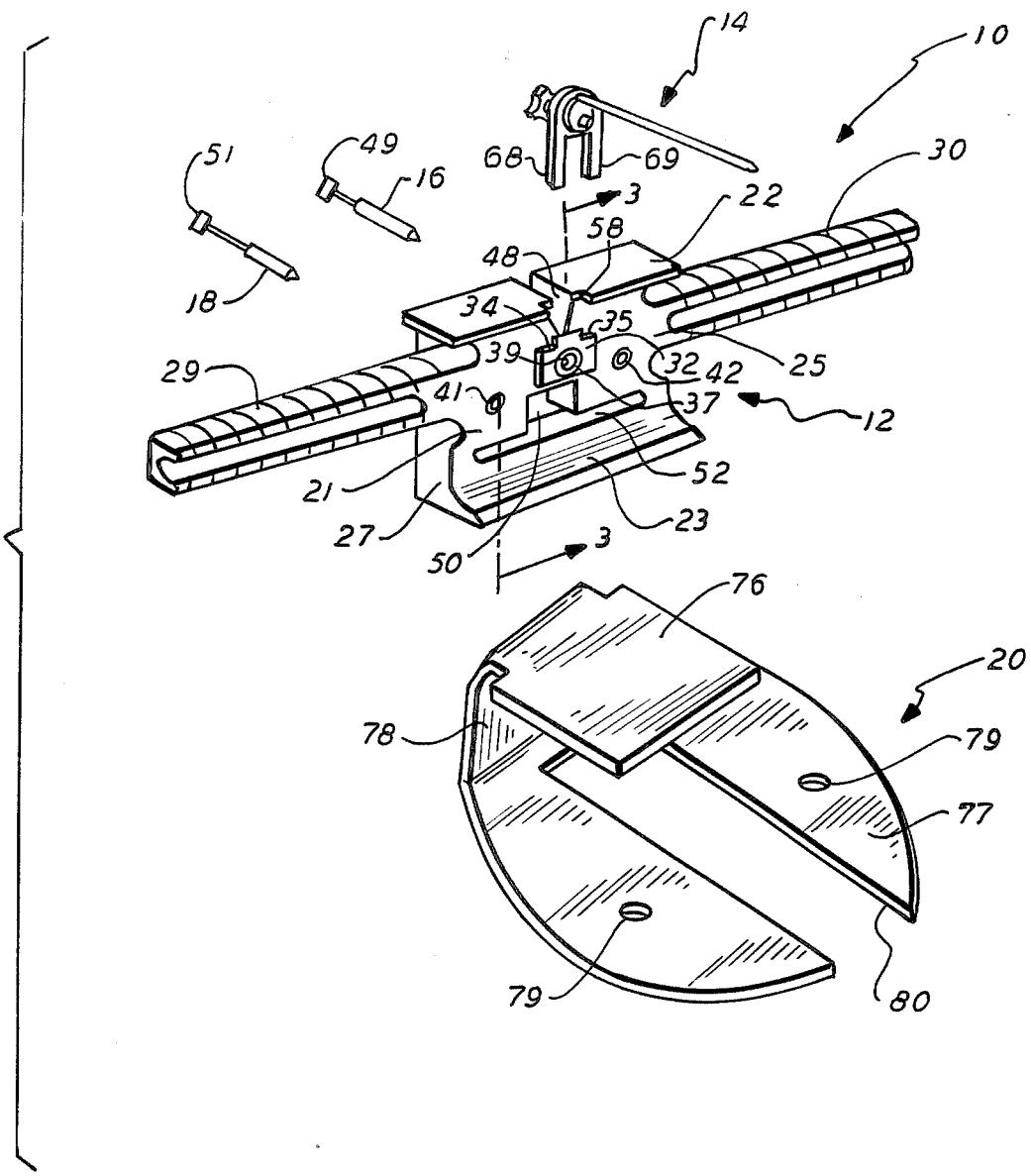
FIG. 1 is a perspective, exploded view of a positioner for surgical instruments structured according to the present invention.

Referring thereto to FIG. 1, an improved femoral resection guide is shown and designated generally by reference numeral 10. Guide 10, shown with its various components in exploded view, can be seen to include a body means 12, a quide means desingated generally by the reference numeral 14, a pair of guide anchoring pins 16 and 18, shown disassembled, and a femoral guide positioner designated generally by the reference numeral 20.

Figure 2:
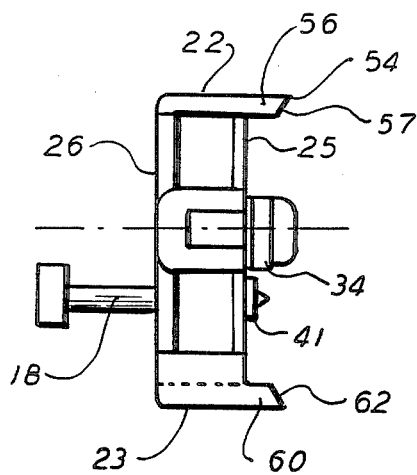
FIG. 2 is an end view of the main body with guide anchoring pins of the positioner of the present invention.
Figure 3:
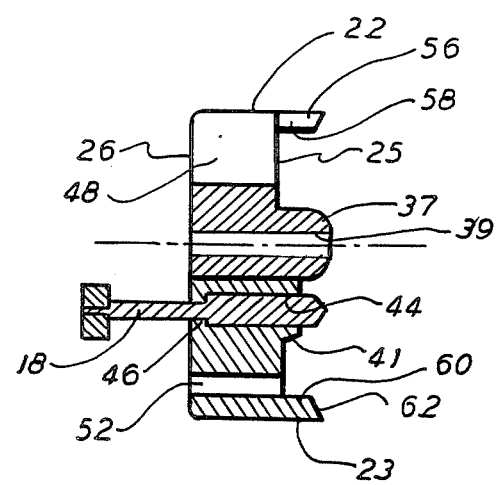
FIG. 3 is an elevational cross-sectional view through the plane 3—3 of FIG. 1.

Considering initially main body 12, and with particular reference to FIGS. 1, 2 and 3, the body can be seen to include a central section 21 having an upper planar surface 22 and a lower planar surface 23. As will become clearer with respect to the detailed description of the use of guide 10, upper planar surface 22 defines the guide for anterior femoral resectioning and lower planar surface 23 defines the guide for posterior femoral resectioning. In the embodiment shown, planar surfaces 22 and 23 are parallel however they may be provided at any predetermined relationship depending upon the particular application for which the instrument is intended to be used.

Central section 21 of main body 12 also includes a rear surface 25, a front surface 26, a first side surface 27 and a second side surface (not visible in the drawings but comprising a mirror of first side surface 27).

Extending outwardly from first side surface 27 along an axis which is generally normal to the plane of the first side surface 27 is a first handle 29. Similarly, extending outwardly from the second side surface 27 and generally coaxially with first handle 29 is a second handle 30. In the embodiment shown, first and second handles 29, 30 are generally U-shaped in cross-sectional configuration and provided with a surface texture which facilitates a firm grip on the instrument by a surgeon during a procedure. In this regard, other handle configurations and surface textures may be utilized within the bounds of suitability surgical procedures, e.g. adaptability for sterilization and the like.

Formed generally centrally in the rear surface 25 of central section 21 is a T-shaped element 32. The base of T-shaped element 32 is secured to rear surface 25 and the cross of T-shaped element 32 is generally parallel to and spaced from rear surface 25. Thus, T-shaped element 32 cooperates with rear surface 25 to define a pair of spaced, vertically extending channels 34, 35. As is discussed below in detail, channels 34 and 35 define a track for slidably receiving guide means 14 therein.

Disposed on the outer surface of T-shaped element 32 is a boss 37. Extending through boss 37, T-shaped element 32 and central section 21 is a through-bore 39. The axis of through-bore 39 is generally normal to the planes of front and rear surfaces 26, 25. As will be discussed below in detail, through-bore 39 defines a drill hole guide means for forming a guide hole in the distal femur of a patient undergoing the procedure.

Also formed on rear surface 25 of central section 21 are a pair of bosses 41 and 42. Extending through boss 41 and central section 21 is a through bore 44 the diameter of which accommodates the sliding reciprocable receipt therein of guide anchoring pin 18. Similarly, extending through boss 42 and central section 21 is a through bore 45 (not shown), the diameter of which accommodates the sliding reciprocable receipt therein of guide anchoring pin 16. Those portions of through-bores 44 and 45 adjacent front surface 26 are provided with inwardly extending annular shoulders 46 and 47 (not shown). Shoulders 46 and 47 cooperate with shoulders formed on pins 16 and 18 to preclude removal of the pins from the bores in a direction from rear surface 25 toward front surfaces 26. Removal of the pins in the direction from front surface 26 to rear surface 25 is precluded by the heads 49 and 51 provided on pins 16 and 18 respectively. Thus, during surgical procedures, pins 16 and 18 are precluded from separation from main body 12 by the limitation on axial movement provided by heads 49 and 51 as well as shoulders 46 and 47. As is discussed below in detail, guide anchoring pins 16, 18 are used to anchor resection guide 10 to a femur such as to maintain positive positioning during resectioning.

Formed in the upper portion of central section 21 is a slot 48. Slot 48 extends through central section 21 from rear surface 25 to front surface 26 and in a direction generally normal to upper planar surface 22 from upper planar surface 22 to a position above through-bore 39. As is discussed below in detail, slot 48 accommodates the mounting of guide means 14 on main body 12.

Also formed in central section 21 below through-bore 39 is a generally T-shaped through-slot 50. The base portion of through-slot 50 defines an access opening and the cross portion 52 of through-slot 50 is dimensioned to slidably receive a mating element of femoral guide positioner 20 therein. In this regard, the upper and lower surfaces of cross portion 52 are planar and generally parallel to the planes of upper and lower planar surfaces 22 and 23 respectively.

As best may be seen in FIGS. 2 and 3, the front edge of upper planar surface 22 is contained in the plane of front surface 26. The rear edge 54 of upper surface 22 is defined by a shoulder 56 which extends outwardly beyond rear surface 25. The rear surface 57 of shoulder 56 is beveled such as to define an angle with respect to the plane of front surface 25. In this regard the angle is such that the plane of surface 57 extends downwardly inwardly as seen in FIGS. 2 and 3 for reasons that are explained below in detail.

Similarly, the front edge of lower planar surface 23 is contained in the plane of front surface 26. The rear edge 59 of lower surface 23 is defined by a shoulder 60 which extends outwardly beyond rear surface 25. The rear surface 62 of shoulder 60 is leveled such as to define an angle with respect to the plane of front surface 25. In this regard the angle is such that the plane of surface 62 extends upwardly inwardly as seen in FIGS. 2 and 3, for reasons that are explained below in detail.

Figure 4:
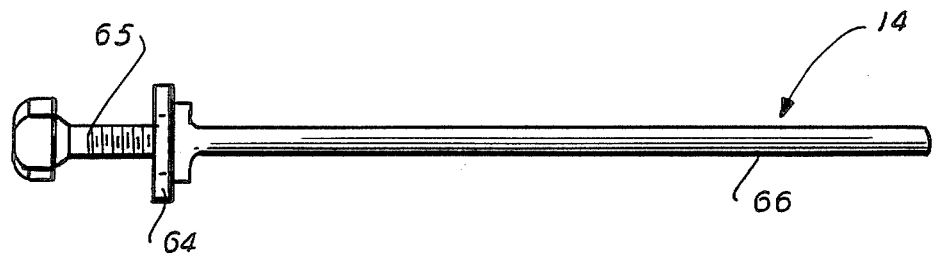
FIG. 4 is a top view of the guide means used with the resectioning guide of the present invention.
Figure 5:
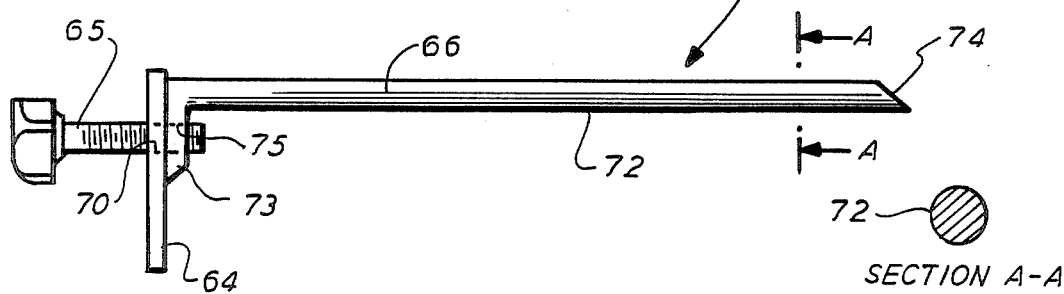
FIG. 5 is a side view of the guide means of FIG. 4.

Considering now alignment bar 14, and with particular reference to FIGS. 4 and 5, guide means 14 can be seen to comprise three elements: guide yoke 64, guide yoke set screw 65 and alignment bar 66. Guide yoke 64 is a generally U-shaped member having a base and first and second generally parallel yoke legs 68 and 69 respectively. The thickness of guide yoke 64 and the spacing of yoke legs 68 and 69 are such as to permit yoke 64 to be slidably received within T-shaped element 32 in main body 12. More specifically, in operating assembled position, first yoke leg 68 is slidably received within channel 34 and second yoke leg 69 is slidably received within channel 35 of T-shaped element 32. Guide yoke 64 is also provided with a tapped through-bore 70 for threadedly receiving guide yoke set screw 65 therethrough.

In the embodiment shown, guide yoke set screw 65 is a standard set screw having an operating head suitable for manual operation. The particular style of set screw may be chosen from any of a number of styles which are generally known in the art.

Alignment bar 66 is an elongated member including a bar portion 72 and a mounting portion 73. As seen in FIG. 5 (Section A—A), the cross-section of bar portion 72 is generally round. The end of bar portion 72 away from mounting portion 73 is tapered to define a beveled surface 74 which facilitates insertion of the alignment bar 66 during the surgical procedure as is discussed below. The mounting portion 73 of alignment bar 66 is secured to the surface of the base of guide yoke 64. Further, mounting portion 73 is provided with a through-bore 75 to accommodate the passage therethrough of guide yoke set screw 65. Thus through-bore 75 and tapped through-bore 70 of guide yoke 64 are coaxial.

Guide anchoring pins 16, 18 are standard anchoring pins having a point formed on one end and a head on the other. The main portion of their shaft diameter is substantially equal to the diameters of through-bores 44 and 45 to permit a sliding fit therethrough. That portion of their shaft diameter between the main portion and the head is reduced such as to define shoulders 46 and 47 to permit physical restraint of the pins during use, all as discussed above.

Femoral guide positioner 20 is a generally U-shaped member having a mating element or connector plate 76, a surface alignment plate 77 and a base connecting portion 78. Formed in surface alignment plate 77 are a pair of through bores 79, the purpose of which is discussed below in detail. Further, surface alignment plate 77 is centrally relieved to define a channel 80 the function of which also is described below in detail.

Figure 6:
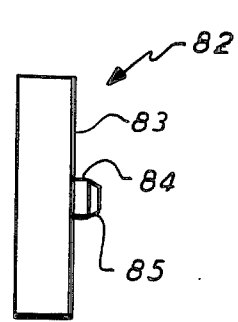
FIG. 6 is a side view of a thickness adaptor plate used with the present invention.
Figure 7:
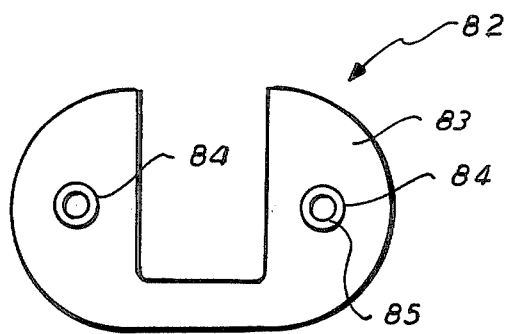
FIG. 7 is a top view of the thickness adaptor plate of FIG. 6.

Referring now to FIGS. 6 and 7, there is shown a thickness adaptor plate designated generally by the reference numeral 82. Thickness adapter plate is flat and shaped generally to correspond to surface alignment plate 77 of femoral guide positioner 20. Formed on surface 83 of plate 82 are a pair of holding pins 84 having beveled edges 85. Pins 84 are positioned in plate 82 such that if plate 82 is aligned with surface alignment plate 77 the axes of pins 84 will be slightly displaced from coaxial with the axes of bores 79 in plate 77. Holding pins 84 are also dimensioned such that insertion of pins 84 within bores 79 will cause displacement of the pins 84 by flexure of bridge 86 to cause coaxial alighment with bores 79 such as to generate a friction fit sufficient to retain the thickness adaptor plate 82 and surface alignment plate 77 in mated position. The function of thickness adapter plate is discussed below in detail.

The various components of the present invention may be manufactured from surgically acceptable materials, e.g. corrosion resistant metal, such as age hardened 17-4 stainless steel or aluminum alloy 6061-T6 using known manufacturing techniques.

Figure 8:
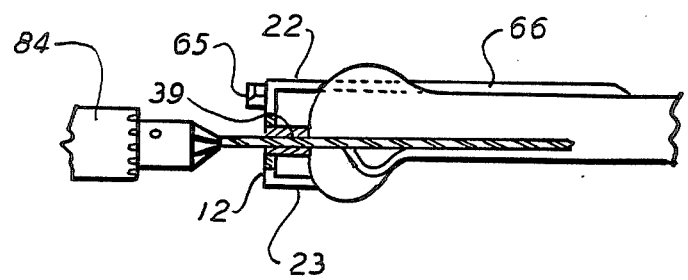
FIG. 8 is a schematic view partially in cross-section of the apparatus of the present invention being used to prepare a femoral grid hole.
Figure 9:
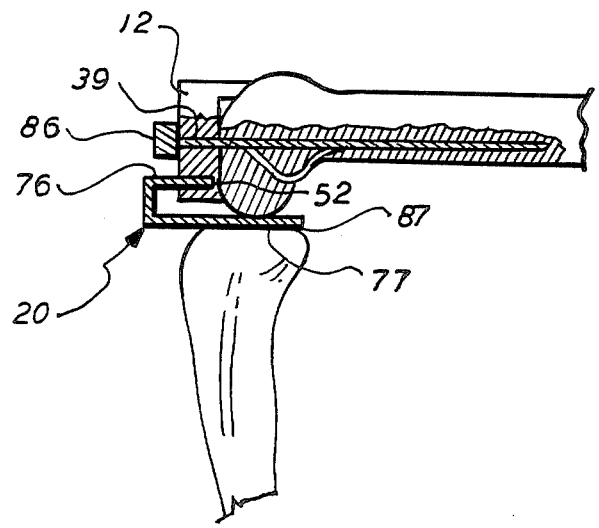
FIG. 9 is a schematic view, partially in cross-section of the resectioning guide of the present invention.

Referring now to FIGS. 8 and 9, the use of the improved femoral resection guide according to the present invention will be described in detail.

As will be recognized by those skilled in these arts, FIG. 8 discloses the distal femur. It will be understood that use of the improved femoral resection guide according to the present invention commences after the complete knee joint has been exposed. For simplicity the schematic view of FIG. 8 is limited to the femur, it being understood that during the first operative step involving the improved femoral resection guide 10 of the present invention, i.e. drilling a femoral guide hole, the tibia and various other knee components are displaced such as to not interfere with the procedure.

Thus, with the knee fully flexed, the surgeon recesses the anterior region of the femoral groove down to the level of the anterior femoral shaft. This provides access for the alignment bar 66 of guide means 14. The guide means 14 is attached to the main body 12 of femoral resectioning guide 10 by sliding yoke legs 68, 69 into channels 34 and 35, respectively, of T-shaped element 32. In this position guide yoke set screw 65 is received within slot 48 such that the operating head is out of contact with rear surface 26.

With the instrument so assembled, the surgeon slides alignment bar 66 under the soft tissue (not shown) overlying the anterior femoral shaft. As the main body 12 approaches the femur, the surgeon centralizes the main body 12 on the distal end of the femur by sliding it up or down the guide means 14. The sliding is achieved by the sliding movement of yoke legs 68 and 69 within channels 34 and 35. Main body 12 is positioned such that the upper planar surface 22 and lower planar surface 23, when used as resectioning guides, will allow approximately equal bone resection of the anterior and posterior femoral surfaces.

With main body 12 positioned as desired, the surgeon tightens guide yoke set screw 65 until the guide means 14 and main body 12 are rigidly engaged and no further relative sliding movement is possible. Thereafter the main body 12 is brought into surface-to-surface contact with the femoral surface.

It should be noted that the beveled rear surfaces 57, 62 of shoulders 56 and 60 respectively approximate the contour of the femoral head and thus assist in the firm positioning of the instrument.

The cooperation of guide yoke 64 with channels 34 and 35 when the structure is set by tightening guide yoke set screw 65 causes the longitudinal axis of alignment bar 66 to be set at a preselected relationship to the axis of through-bore 39. In the disclosed preferred embodiment the established relationship is parallelism. Thus the guide yoke structure defines an axial reference with respect to which the body 12 may be positioned to act as a guide or positioner for other instruments utilized to invade the femur.

With the instrument so positioned, a drill 84 (FIG. 8) of appropriate size, e.g. one quarter inch, is introduced through through-bore 39 of main body 12, which through-bore acts as the drill guide for drilling of the femoral guide hole. The hole is drilled in the femur whereafter the main body 12 and guiee means 14 are removed in anticipation of the next step of the procedure.

The instrument of FIG. 1 shows the alignment axis as being referred with respect to the anterior surface of the distal femur. However other characteristics of the femur may be established as a reference characteristic.

In this regard, the next step of the procedure involves resection of the tibial articular surface. This resectioning is accomplished through the use of a tibial resection guide according to procedures for performing the tibial articular surface resection all as fully disclosed in the DePuy publication identified above.

Once the reaction of the tibial articular surface is complete, the tibial resection guide is removed and the main body 12 of the femoral resection guide is placed on the femur and located thereon by alignment rod 86 which extends through through-bore 39 into the guide hole which previously was formed in the femoral shaft.

For the total knee replacement being described with respect to the preferred embodiments it is desirable that the upper planar surface 22 and the lower planar surface 23 of main body 12, which are to act as the anterior and posterior femoral resection guide surfaces, respectively, be parallel to the resected surfaces, respectively, be parallel to the resected surface 87 of the tibia in the flexed position of the knee when the axial orientation and location of the femur relative to the tibia is such that proper ligamentous tension, established during the surgical procedure when the tibial resection was performed, is reproduced. To this end femoral guide positioner 20 is assembled to main body 12 by sliding mating element 76 into the cross-portion 52 of through-slot 50 in main body 12. At the same time, the lower surface of alignment plate 77 is brought into surface-to-surface contact with the resected tibial surface 87 as shown in FIG. 9. Because the plane of mating element 76 is parallel to the plane of the lower surface of alignment plate 77, and further because the upper and lower surfaces of slot 52 are in surface-to-surface contact with the upper and lower surfaces of mating element 76, and further because the plane of slot 52 is parallel to the planes of upper and lower planes surface 22 and 23, and still further since the distance from the axis of the alignment rod 86 to the interior surface 88 of the alighment plate 77 of the femoral guide positioner 20 is similar to the distance between the same alighment rod and the most superior guiding surface of the tibial resection guide described in the publication cited above and in copending application Ser. No. 06-587,263 dated Mar. 7, 1984 (differing only by the amount of saw tooth offset, i.e. height pf the tooth above the surface of the blade) the maintenance of the resected tibial surface 86 in surface-to-surface contact with plate 77 will result in planar surfaces 22 and 23 being parallel to resected tibial surface 87 and the maintenance of the ligamentous tension established earlier. Thus, anterior and posterior resectioning of the distal femur using surfaces 22 and 23 as resection guides will result in resected anterior and posterior femoral surfaces which are parallel to resected tibial surface 87 in the pre-selected flexed orientation with properly established ligamentous tension in the flexed position. Furthermore, since said abovementioned distance introduces a space between the posterior femoral resection plane and the tibial resection plane 87 corresponding to the dimensions of the prosthetic components occupying this space after component implantation the ligamentous tension in flexion selected during the tibial resection will be reproduced after prosthesis implantation.

Where tibial resection is performed using the lower to guide slots of said Tibial Resection Guide the increase in said distance between the axis of the alignment rod 86 and the resected tibial surface 87 is accommodated by the use of a thickness adaptor plate 87 the thickness of which is equal to the distance between the upper guide slot and the slot used for the tibial resection.

The parallel resected surface with reproduction of ligamentous tension in flexion relationship as described above have been found to contribute significantly to the overall success of the total bone replacements utilizing the instrument of the present invention.

The remaining steps of the total bone replacement procedure are described in detail in the DePuy publication identified above. The foregoing, however, discloses in detail the structures and use of an improved femoral resection guide according to the present invention. It will be recognized by those skilled in the arts, however that modifications and variations to the structure of the described preferred embodiment may be made without departing from the spirit and scope of the invention.

What is claimed is:
1. A positioner for surgical instruments used to invade a bone, comprising:
   a body means, said body means including at least one guide surface for positioning a resectioning surgical instrument for resectioning a first bone;
   an alignment plate secured to said body means, said alignment plate including a planar reference surface for engaging in surface-to-surface contact with a surface on a second bone defining a reference plane, said planar reference surface being in a desired geometric relationship with said one guide surface on said body means, and wherein said first bone and said second bone are joined by ligaments, said alignment plate including means for spacing said first bone with respect to said second bone to establish a desired ligamentous tension; and
   an alignment rod means disposed on said body means, said alignment rod means for engaging said first bone to cooperate with said alignment plate to space said first and second bones to establish said desired ligamentous tension wherein said alignment rod means is slidably received within a bore formed axially in said first bone and said first bone is rotatable with respect to said body means on said alignment rod means.

* * * * *